(12) United States Patent
Botticini et al.

(10) Patent No.: US 8,512,281 B2
(45) Date of Patent: Aug. 20, 2013

(54) ANGIOPLASTY MEDICAL DEVICES MADE OF ELASTOMERIC MATERIAL

(75) Inventors: Cesare Botticini, Concesio (IT); Paolo Pellegrini, Rovato (IT)

(73) Assignee: Medtronic, Inc., Minneapolis, MN (US)

( * ) Notice: Subject to any disclaimer, the term of this patent is extended or adjusted under 35 U.S.C. 154(b) by 411 days.

(21) Appl. No.: 12/300,475

(22) PCT Filed: May 12, 2006

(86) PCT No.: PCT/IT2006/000355
§ 371 (c)(1),
(2), (4) Date: Nov. 12, 2008

(87) PCT Pub. No.: WO2007/132485
PCT Pub. Date: Nov. 22, 2007

(65) Prior Publication Data
US 2009/0187145 A1 Jul. 23, 2009

(51) Int. Cl.
*A61M 29/00* (2006.01)

(52) U.S. Cl.
USPC ............... 604/96.01; 264/209.3; 264/331.19; 528/310

(58) Field of Classification Search
USPC ...... 264/209.3, 331.19; 528/310; 604/96.01, 604/98.01, 101.04
See application file for complete search history.

(56) References Cited

U.S. PATENT DOCUMENTS

| 5,585,057 | A | | 12/1996 | Trotta |
| 5,763,561 | A | * | 6/1998 | Keske ........................... 528/310 |
| 6,036,697 | A | | 3/2000 | DiCaprio |
| 6,110,142 | A | * | 8/2000 | Pinchuk et al. ............ 604/96.01 |
| 6,200,290 | B1 | | 3/2001 | Burgmeier |
| 6,592,550 | B1 | | 7/2003 | Boatman et al. |
| 7,029,732 | B2 | | 4/2006 | Wang et al. |
| 7,749,585 | B2 | * | 7/2010 | Zamore ........................ 428/35.1 |
| 2002/0132072 | A1 | | 9/2002 | Wang et al. |
| 2004/0048016 | A1 | | 3/2004 | Wang et al. |

FOREIGN PATENT DOCUMENTS

| EP | 1314750 | 5/2003 |
| EP | 1482011 | 12/2004 |

* cited by examiner

*Primary Examiner* — Gregory Listvoyb

(57) ABSTRACT

The present invention relates to a medical device for angioplasty or parts thereof, which is made of elastomeric material, wherein the elastomeric material comprises a polyamide-based polymer obtained from the polymerization of a compound forming polyamide blocks that is selected from the group consisting of an aminocarboxylic acid of Formula (1) and a lactam of Formula (2):

$$H_2N-R1-COOH \quad (1)$$

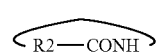

(2)

with a polyether diamine triblock compound of Formula (3):

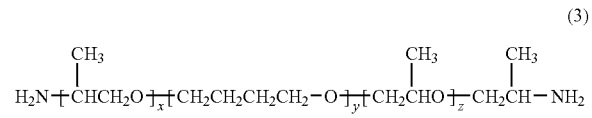

(3)

and a dicarboxylic acid of Formula (4):

$$HOOC-(R3)_m-COOH \quad (4)$$

wherein the groups R1, R2 and R3 are each binding groups comprising a hydrocarbon chain therein that may be interrupted by one or more amide groups; x is an integer from 1 to 20; y is an integer from 4 to 50, z is an integer from 1 to 20; m is 0 or 1.

25 Claims, No Drawings

ANGIOPLASTY MEDICAL DEVICES MADE OF ELASTOMERIC MATERIAL

FIELD OF THE INVENTION

The present invention relates to the use of a material for angioplasty medical devices, particularly for angioplasty catheters and more particularly for balloons placed at a catheter distal end.

BACKGROUND ART

The use of catheters in angioplasty is widely known. A catheter provided with a balloon at the distal end thereof is advanced, by following a guide wire, to the ostium of the narrowed artery. When the balloon has been placed at the narrowing of the artery, it is repeatedly inflated and deflated. The insufflation, with subsequent deflation, of the balloon within the artery reduces the amount of narrowing of the arterial lumen and restores a suitable blood flow within the heart region, which is diseased because of the stenosis.

The chemical-physical and mechanical characteristics of the plastic material of which the balloon is made determine its compliance, i.e. the adaptability of the balloon to the arterial system, and the resistance to deployment, which are primary characteristics for an optimum operation of the balloon. The compliance and resistance requirements, and the size of the balloon may vary according to the type of use and size of the vessel in which the catheter is delivered. The advantages offered by the various polymers are correlated to the particular mechanical applications of the balloons.

SUMMARY OF THE INVENTION

The problem addressed by the present invention is to provide angioplasty medical devices or parts thereof having improved physical characteristics as compared with those of the prior art. Particularly, the present invention aims to solve the problem of achieving angioplasty catheters, more particularly parts of the same, such as outer tubes, tips and balloons, which are made of a flexible material that is also provided with a high degree of resistance.

The object of the present invention is the use of a constitutive material for angioplasty medical devices and particularly for catheters or parts thereof, such as balloons, tubes and tips, such as defined in the annexed claims, whose definitions are integral part of the present description.

Further characteristics and the advantages of the medical devices being the object of the present invention will appear more clearly from the following detailed description of the invention.

DETAILED DESCRIPTION OF THE INVENTION

In an embodiment, the angioplasty medical devices, and particularly, catheters or parts thereof, preferably catheters balloons, are made of a polyamide-based thermoplastic elastomer.

This elastomer comprises monomers forming polyamide blocks, which are the hard portion of the material, modified with a group which is the soft part.

This elastomer is obtained by polymerizing a compound forming polyamide blocks selected from the group consisting of an aminocarboxylic acid such as of Formula (1) and a lactam such as of Formula (2):

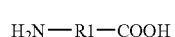

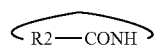

with a triblock polyetherdiamine compound of Formula (3):

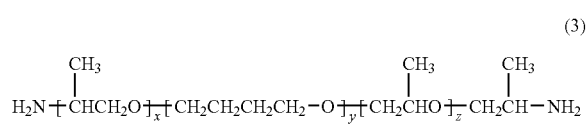

and a dicarboxylic acid such as of Formula (4):

$$HOOC-(R3)_m\text{-}COOH \quad (4)$$

In said formulae, the groups R1, R2 and R3 are each binding groups comprising a hydrocarbon chain therein, which may be interrupted by one or more amide groups. Preferably, R1 and R2 comprise independently an alchilene group having 2 to 20 carbon atoms and amide bonds and R3 comprises an alkylene group having 1 to 20 carbon atoms.

x may change from 1 to 20, preferably from 1 to 18, more preferably from 1 to 16; y may change from 4 to 50, preferably from 5 to 45, more preferably from 8 to 30 and z may change from 1 to 20, preferably from 1 to 18, more preferably from 1 to 12;

m is 0 or 1.

Generally, the polymerization is carried out using 15 to 70 wt % of the compound of Formula (1) and/or (2) and a mixture of compounds of Formulae (3) and (4) having a total weight ranging between 30 and 85%. This polymerization is carried out in a reactor at a temperature ranging between 150 and 300° C., preferably between 160 and 280° C., more preferably between 180 and 250° C.

The polymerization can be carried out according to two different methods:

the first method is inserting in the reactor the components of Formula (1) and/or (2), the component of Formula (3) and the component of Formula (4), heating and adjusting the pressure to complete polymerization. The second synthetic method provides a pre-polymerization between the components of Formula (1) and/or (2) with the component from Formula (4), and subsequent addition within the reactor of the component of Formula (3) to complete polymerization.

In both cases, the polymerization may be carried out in a batch-loaded vessel or in a continuous reactor (PFR).

The aminocarboxylic acids of Formula (1) and the lactams of Formula (2) may be aliphatic, alicyclic or aromatic, for example they can be obtained from the reaction between diamines and dicarboxylic acids and salts thereof. The diamines and the dicarboxylic acids can be aliphatic, alicyclic and aromatic. Preferably, the diamines and the dicarboxylic acids are aliphatic.

Examples of diamine compounds include diamines having 2 to 20 carbon atoms, such as ethylendiamine, triethylene diamine, tetramethylene diamine, hexa-, hepta-, octa-, nona-, deca-, undeca-, dodeca-methylene diamine, 2,2,4-trimethyl hexamethylene diamine, 2,4,4-trimethyl hexamethylene diamine and 3-methyl hexamethylene diamine.

Examples of dicarboxylic acids include dicarboxylic acids having 2 to 20 carbon atoms, such as oxalic acid, succinic acid, glutaric acid, adipic acid, azelaic acid, etc. Alternatively, the dicarboxylic acid (4) may be synthesized by dimerization of unsaturated fatty acids. Examples of these unsaturated fatty acids are: Pripol 1004, Pripol 1006, Pripol 1009 and Pripol 1013 sold by Unichema North America, Chicago, Ill., USA.

Examples of lactams include compounds having 5 to 20 carbon atoms, such as ε-caprolactam, ω-enantholactam, ω-undeca-lactam, 2-pyrrolidone, etc.

Examples of amino-carboxylic acids include aliphatic ω-aminocarboxylic acids having 5 to 20 carbon atoms, such as 6-aminocaproic acid, 7-aminoheptanoic acid, 8-aminooctanoic acid, 10-aminocapric acid, 11-aminoundecanoic acid and 12-aminododecanoic acid.

The polyamide segment is preferably selected from PA 6, PA 6/6, PA 6/9, PA 6/10, PA 6/12, PA 6/36, PA 11, PA 12, PA 12/12. Furthermore, copolyamides or multipolyamides are preferably used, which are obtained from $C_2$-$C_{36}$ dicarboxylic acids and $C_2$-$C_{12}$ diamines as well as lactam 6, lactam 12, isophtalic, terephtalic and naphthalene dicarboxylic acids.

The polyamide segments can be also obtained from monomers of $C_6$-$C_{12}$ lactams or monomers of $C_6$-$C_{12}$ aminocarboxylic acids. The polyamide component can also be obtained from the polycondensation of the corresponding diamine salts and carboxylic acids as described above. By changing x, y and z in the polyether diamine triblock compound (Pe) of formula (3):

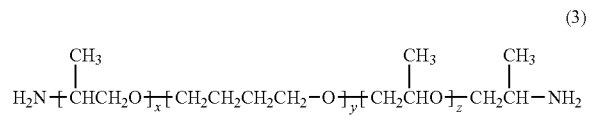

(3)

a material is obtained, which has different physical characteristics.

If the material is required to be highly transparent, x must range between 2 and 6, preferably between 3 and 4; y must range between 6 and 12, preferably between 8 and 10; z must range between 1 and 5, preferably between 2 and 3.

On the other hand, if the material is required to have high stress resistance, x must range between 2 and 10, preferably between 2 and 6; y must range between 13 and 28, preferably between 13 and 21; z must range between 1 and 9, preferably between 1 and 5.

The poly-ether diamine triblock compound of Formula (3) being used can be identified as a polyether diamine triblock XYX. This group is sold by HUNTSMAN Corp., USA: with the code XTJ-533 is identified a compound in which x is approximatively equal to 12, y is approximatively equal to 11 and z is approximatively equal to 11. With the code XTJ-536 is identified the material in which x is approximatively equal to 9, y is approximatively equal to 17 and z is approximatively equal to 8. With the code XTJ-542 is identified the material in which x is approximatively equal to 3, y is approximatively equal to 9 and z is approximatively equal to 2.

Three preferred compositions of the polyether diamine triblock compound are reported in Table 1 below:

TABLE 1

| name | x | Y | z |
|---|---|---|---|
| XYX-1 | 3 | 14 | 2 |
| XYX-2 | 5 | 14 | 4 |
| XYX-3 | 3 | 19 | 2 |

Preferably, the polyamide-based polymer is represented by the general formula (5):

$$HO-(OC-PA-CO-HN-Pe-NH)_n-H \quad (5)$$

wherein PA is the polyamide portion and Pe the soft portion, i.e. a polyether portion, whereas n is the number of units forming the polymer.

This polymer has a molecular weight ranging between 19000 and 50000.

The polymers described above and used in the present invention to obtain medical devices for angioplasty are for example sold under the name of UBESTA XPA™ by UBE INDUSTRIES, LTD. Examples of particularly suitable commercially available polymers are UBESTA XPA 9055™, UBESTA XPA 9063™, UBESTA XPA 9044™, UBESTA XPA 9070™.

The hardness of the material such as measured using the Shore D scale is indicated by the last two digits of the numeric code following the wording UBESTA XPA. Different materials will be thus used for different uses, according to the desired hardness and flexibility, by mixing them together either with the addition of polyamide or not.

The polyamide-based polymer of the present invention may be used as such for manufacturing medical devices for angioplasty, particularly for catheter balloons, or a mechanical mixture of the same also including polyamide in the mixture may be used. In the latter case, the polyamide-based polymer is comprised in the mixture from 10 to 90 wt %, preferably 75 to 25%, more preferably 60 to 40 wt %, the remaining part of the mixture being polyamide.

The polyamide used in these mixtures is selected from the group consisting of: PA 6, PA 6/6, PA 6/9, PA 6/10, PA 6/12, PA 6/36, PA 11, PA 12 and PA 12/12. Preferably, it is polyamide 12.

The resulting compound will have mechanical characteristics mediated between those of its basic components.

The medical devices for angioplasty, particularly catheters and more particularly catheter balloons obtained with the inventive material exhibit improved physical characteristics as compared with the medical devices, particularly catheter balloons that are obtained with materials known in the art, such as pebax, which is manufactured by Arkema, and grilamid FE7303, manufactured by EMS. These improved characteristics are illustrated herein below also by means of comparative examples.

The balloons obtained with the elastomeric material described in the present invention, in fact, have an optimum characteristic of high flexibility and elasticity. In fact, considering that by flexibility of a material is meant the capacity of this material to return to its original shape after its initial shape has been temporarily changed by a deformation, it is understood that a balloon made of a very flexible material will easily withstand the mechanical stress caused by the repeated action of inflation and deflation which is required during an angioplasty operation.

Furthermore, it has been surprisingly found that the balloon made of elastomeric material being the object of the present invention has an optimum compliance characteristic, which is meant as a percentage increase in the balloon diameter following pressure increase, in addition to an optimum characteristic of adaptability to the arteries and resistance to deployment.

This combination of the characteristics of good flexibility on the one side, and optimum compliance and resistance on the other side characterizes the balloons of the present invention and is further a combination of basic features for a balloon which is delivered in a patient's arterial system during the angioplasty treatment.

The compliance test is carried out by measuring the diameter increase (in mm) of the balloon being tested as compared with the pressure increase (in bars) to burst pressure.

With this experiment it has also been possible to ascertain that a lower average thickness can be maintained in the balloon wall as compared with normal thicknesses of prior art balloons, by maintaining high burst pressure values. Consequently, with the same balloon diameter, a lower wall thickness, i.e. a lower amount of material, can be used as compared with prior art, while still maintaining high burst pressure levels (RBP). As a consequence, this characteristic of the inventive material results in the great advantage that balloons can be used, which are provided with a smaller profile which requires smaller delivery devices, thereby the delivery of the catheter and delivery device in the arterial system is less traumatic for the patient.

This characteristic is particularly advantageous also with coronary medical balloons, which require high flexibility, compliance and low thickness, mainly with coronary total occlusion (CTO). In this case, in fact, the artery is almost completely blocked by one or more stenosis, and catheters must be used, which are provided with a high RBP rate (Rate Burst Pressure), low thickness of the balloon wall and high tensile at break rate, i.e. which are capable of being delivered within the small cavity between the stenosis and withstanding high inflating pressures.

The sum of these characteristics has been surprisingly found using the elastomeric material of this invention, either taken as such or mixed with polyamide.

Due to the good flexibility, the balloon according to the present invention also has a good manoeuvrability. In fact, the elastomeric material also has a good capacity of following the trace and a good adaptation to the vessel path. Accordingly, this characteristic also improves the capacity of advancing the catheter, the balloon being placed at the distal end thereof, along the vessel system to reach the stenosis lesion. When the narrowing of the artery has been obtained, the good flexibility of the balloon also provides the non-insufflated balloon with improved capacity to be placed at the stenosis obstruction. The improved adaptability of the material facilitates the passage of the non-insufflated balloon through the narrowed arterial region. This facilitated passage of the balloon through the venous pathway and through the stenosis lesion finally ensures a lower risk of causing further damages both to the venous system involved and stenosis lesion.

The good characteristics of flexibility and elasticity of the balloon of the present invention then allow to obtain balloons, which are advantageously characterized by an improved "return-behaviour" to the original diameter size, after each subsequent insufflation. This allows one to use the same balloon for a greater number and longer duration of insufflations. The flexibility is measured by means of a bounce flexibility test of balloon tubes. The test has been carried out according to the standards as reported by the International Organization for Standardization and described in the standard ISO 14630: 1997. A balloon tube having 0.9 mm outer diameter is positioned by fixing the same to a support equipment, such that 0.15 mm operating length is obtained. The tip of a feeler that is connected to a dynamometer is just leant against the surface of said balloon-tube. This feeler is lowered to contact the tube and the force is measured, which is required to obtain a certain lowering amount for the feeler. The lowering speed of the feeler is 20 mm/min.

The good behaviour of the balloon with respect to wear further derives from high flexibility. In fact, during normal use of the angioplasty balloons, the breaking pressure of the balloon is reduced throughout subsequent repeated insufflations. On the other hand, the good flexibility of the balloon made of elastomeric material of the present invention improves the capacity of maintaining the value of breaking pressure as determined for the new balloon. This characteristic also allows using the balloon according to the present invention for a greater number of insufflations and a longer duration of the same.

A further advantage of the balloons obtained with an elastomeric material of the present invention is the good behaviour of the balloon in the tensile test.

A test has been carried out on the balloons of the present invention aiming at evaluating the force required to cause the balloon to break by means of tensile stress. This test has been also carried out according to the standards as reported by the International Organization for Standardization and described in the standard ISO 14630: 1997. To carry out the test, the balloons are attached at the one end thereof to a fixed clamp, and at the other end to a mobile cross-piece which moves at a speed of 50 mm/min, the balloon being elongated to break. The elongation of the balloon is calculated along with the respective yield load until a peak load is reached, which is the breaking point of the balloon and then the corresponding breaking load.

Due to its high flexibility, a further advantage of the material described herein is an improved manoeuvrability of all the catheter, when applied to various catheter portions, such as inner tube, outer tube, tip. In fact, the catheter portions made of elastomeric material according to the present invention provide the catheter with a good capacity of following the trace and a good adaptation to the vessel pathway.

Another advantage of using the material described herein applied to angioplasty balloons is the characteristic of high viscosity of this material and the capacity of maintaining a high viscosity level also over time. This advantage is particularly seen in the material's good fluidity behaviour during the extrusion process to form the tube, from which the balloon is then obtained. Accordingly, the elastomeric material described in the present invention does not require the polyamide formulation to be added with plasticizers as adjuvants.

A further advantage of the elastomeric material described herein is the low water absorption in aqueous solutions. In fact, polymer substances are known to absorb water and thus tend to swell. The polymers of the present invention, on the contrary, due to low water absorption do not tend to swell and thus exhibit very low weight and volume increase in aqueous solutions, their shape, volume and size remaining unchanged.

This characteristic is also very advantageous mainly during the step of extruding the tube from which the balloon is obtained. In fact, before extrusion, all the materials must be put in an oven to lose the residual humidity of the grains. A polymer material that exhibits a low water absorption thus requires, firstly, a shorter pre-drying time. Furthermore, during the extrusion step, the tube protruding from the die is passed through calibration and cooling tanks containing water. The greater the amount of water that the polymer tube tends to absorb, the greater the risk that micro-cavities are formed within the tube wall and consequently micro-cavities within the balloon wall. These micro-cavities are sudden variations in the thickness of the balloon wall and thus are likely to be breakage weak points in the balloon.

Furthermore, it should be noted that the elastomeric material as described in the present invention has a high chemical resistance to hydrolysis in aqueous milieu. This chemical stability to hydrolytic degradation contributes to increase the shelf life of the balloon obtained with said material, since it ensures that the particular mechanical characteristics of the balloon are maintained over time.

The production of tubes for processing the elastomeric material being the object of the present invention can be carried out by means of one of a number of extrusion or pultrusion techniques, which are well known to those skilled in the art, at temperatures ranging between 150° and 350° C.

Particularly, the tubes intended for manufacturing the balloons described herein have been made by extruding the elastomeric material being the object of the present invention by means of single-screw extruders, at temperatures ranging between 200° C. and 250° C.

Other extrusion temperatures can be used when the plant characteristics and ratios of the individual components of the elastomeric material being the object of the present invention are changed.

The invention is further described by means of the following examples, which are referred only to the balloons, by way of non-limiting illustrations thereof, from which the characteristics and advantages of the present invention will appear even more clearly.

To carry out the tests, different material mixtures have been arranged.

The following example demonstrate with comparative tests that the medical devices for angioplasty of the invention, preferably catheters or parts thereof, have the above-mentioned improved characteristics as compared with the devices made of known materials, such as grilamid FE7303.

EXAMPLE 1

The first tested mixture consists of 40 wt % Polyamide 12 and 60 wt % UBESTA XPA 9063™.

Several physical characteristics of mixture 1 are reported in Table 2:

TABLE 2

| Characteristic | Method | Unit | mixture of 40% PA12-60% UBESTA XPA 9063 |
|---|---|---|---|
| Melting Point | ISO 11357 | ° C. | 164 (UBESTA XPA 9063)-178 (PA12) |
| Glass transition temperature | ISO 11357 | ° C. | −56 |
| MVR | ASTM 1238 (215° C., 2.16 Kg) | ml/min | 7.3 |
| tensile strength | ASTM D638 | Mpa | 38.34 |
| Tensile Elongation | ASTM D638 | % | 450 |
| Flexural elastic modulus | ASTM D790 | Mpa | 713 |
| Hardness | ASTM D2240 | Shore D | 67.5 |
| Heat distortion temperature under 0.46 Mpa load | ASTM D648 | ° C. | 106 |

Table 3, reported herein below, shows the data obtained from a flexural test that is carried on extruded tubes, from which the balloons are subsequently obtained, which are made of elastomeric material according to the present invention. The tubes used have 0.70 mm outer diameter and 0.40 mm inner diameter. This test confirms the characteristic of high flexibility of the material described above. In Table 3 there are reported the load values (expressed in Newtons), which are obtained at preset lowering amounts for the feeler (1 to 8 mm).

TABLE 3

| | | Cross-beam displacement | | | | | | | |
|---|---|---|---|---|---|---|---|---|---|
| Sample | | 1 mm | 2 mm | 3 mm | 4 mm | 5 mm | 6 mm | 7 mm | 8 mm |
| Load (N) | 1 | 0.015 | 0.021 | 0.024 | 0.028 | 0.031 | 0.032 | 0.034 | 0.035 |
| | 2 | 0.014 | 0.018 | 0.020 | 0.021 | 0.023 | 0.025 | 0.028 | 0.026 |
| | 3 | 0.017 | 0.021 | 0.024 | 0.028 | 0.029 | 0.030 | 0.032 | 0.032 |
| | 4 | 0.019 | 0.023 | 0.028 | 0.032 | 0.029 | 0.035 | 0.036 | 0.036 |
| | 5 | 0.016 | 0.023 | 0.028 | 0.029 | 0.030 | 0.033 | 0.034 | 0.033 |
| Average | | 0.016 | 0.021 | 0.025 | 0.028 | 0.029 | 0.031 | 0.033 | 0.032 |

The table shows a maximum load point of 0.036 N at 7-8 mm feeler travel. This result is particularly significant as it points out the optimal flexural characteristic of the inventive material.

To better appreciate the high flexibility of the tube made of elastomeric material according to the present invention, a comparative test has been carried out with equally sized tubes made of prior art Grilamid® FE7303. The results are reported in Table 4:

TABLE 4

| | Displacement of cross-beam | mixture 1 average values | grilamid FE7303 average values |
|---|---|---|---|
| Load (N) | 1 mm | 0.016 | 0.026 |
| | 2 mm | 0.021 | 0.031 |
| | 3 mm | 0.025 | 0.035 |
| | 4 mm | 0.028 | 0.038 |
| | 5 mm | 0.029 | 0.042 |
| | 6 mm | 0.031 | 0.044 |
| | 7 mm | 0.033 | 0.044 |
| | 8 mm | 0.032 | 0042 |
| Maximum load | | 0.033 | 0.044 |

Tubes having the same size have been used for the comparative test. The wall thickness is 0.15 mm. The various materials have the same degree of hardness. As may be seen in Table 4, the material from mixture 1 of the invention has a maximum load, at the same travel of the feeler, which is lower than the known material, and consequently an improved flexibility as compared with grilamid.

A tube made of material from mixture 1 has 67.5 Shore D hardness, 713 Mpa flexural elastic modulus, 38.34 Mpa tensile strength at break and about 450% elongation at break. With grilamid FE7303, the comparative tests have demonstrated Shore D values, flexural elastic modulus and tensile strength at break comparable with those of mixture 1, whereas the elongation at break is about 300%. Consequently, the inventive mixture 1 has an improved capacity of elongation as compared with the known product.

In the compliance and flexibility tests, 31 balloon samples have been tested having 1.25 mm outer diameter at 6 bar rated pressure, with 0.02 double average wall thickness.

The compliance test is carried out by measuring the diameter increase (in mm) of the balloon being tested as compared with the pressure increase (in bars) to burst pressure.

The most significant data obtained from this test are reported in Table 5. The reported data relate to the average burst pressure recorded, the standard deviation of the measurements performed and the RBP (Rated Burst Pressure) calculated.

TABLE 5

| Balloon diameter | 1.25 |
| --- | --- |
| Double average wall thickness | 0.020 |
| Average burst pressure (bar) | 23.04 |
| Standard deviation | 0.85 |
| Calculated RBP (bar) | 18.68 |

The following Table 6 shows the results obtained from comparative measurement tests of "average burst pressure" and "calculated burst pressure" with the same balloon diameter and double average wall thickness, between the mixture 1 of the invention and grilamid FE7303.

TABLE 6

| | mixture 1 | | | Grilamid FE7303 | | |
| --- | --- | --- | --- | --- | --- | --- |
| Balloon diameter | Double average wall thickness (mm) | Average burst pressure (bar) | Burst pressure calculated (RBP) | Double average wall thickness (mm) | Average burst pressure (bar) | Burst pressure calculated (RBP) |
| 1.50 | 0.020 | 21.55 | 16.65 | 0.024 | 18.23 | 14.27 |
| 2.00 | 0.030 | 24.94 | 21.11 | 0.034 | 22.80 | 19.57 |
| 2.50 | 0.032 | 19.15 | 16.54 | 0.038 | 19.95 | 14.03 |
| 3.00 | 0.038 | 22.88 | 20.90 | 0.042 | 22.96 | 18.50 |

As may be seen in Table 6, with the same balloon diameter, the inventive material allows having a lower wall thickness while maintaining good burst pressure levels, as compared with the known product. This entails great advantages in terms of applications, which have been explained above.

A further advantage of the balloons obtained with the elastomeric material from mixture 1 is the optimum behaviour during the tensile test. To better appreciate this aspect, comparative tests have been carried out using balloons obtained with mixture 1 and balloons obtained from grilamid FE7303. The data obtained are reported in Table 7.

TABLE 7

| | Load (N) | % Elongation |
| --- | --- | --- |
| Mixture 1 | 9.1 | 50 |
| Grilamid FE7303 | 2.6 | 20 |

As may be seen from the data reported in Table 7, the balloons obtained with the elastomeric material of mixture 1 are considerably more resistant and have a percentage elongation at break equal to about twice those obtained with prior art materials.

The load expressed in Newton represents the tensile stress to be applied to break the balloon.

The mixture 1 is particularly advantageous for the extrusion of coronary medical balloons, which require high flexibility and compliance, mainly with coronary total occlusion (CTO). At the same time, a high RBP value (Rate Burst Pressure) is required, while maintaining a low thickness of the balloon wall and a high tensile at break value. The sum of these characteristics has been surprisingly found using the elastomeric material of this invention, either taken as such or mixed with polyamide.

EXAMPLE 2

The second mixture consists of 60 wt % Polyamide and 40 wt % UBESTA XPA 9063™.

Several physical characteristics of mixture 2 are reported in Table 8:

TABLE 8

| Characteristic | Method | Unit | mixture of 60% PA12-40% UBESTA XPA 9063 |
| --- | --- | --- | --- |
| Melting Point | ISO 11357 | ° C. | 164 (UBESTA XPA 9063)-178 (PA12) |
| Glass transition temperature | ISO 11357 | ° C. | −56 |
| MVR | ASTM 1238 (215° C., 2.16 Kg) | ml (min) | 3.5 |
| Tensile strength | ASTM D638 | Mpa | 46.17 |
| Tensile Elongation | ASTM D638 | % | 350 |
| Flexural elastic modulus | ASTM D790 | Mpa | 1066 |
| Hardness | ASTM D2240 | Shore D | 70.5 |
| Heat distortion temperature under 0.46 Mpa load | ASTM D648 | ° C. | 120 |

Table 9, reported herein below, shows the data obtained from a flexural test that is carried on extruded tubes made of elastomeric material according to the present invention from which the balloons are subsequently obtained. The tubes used have 0.90 mm outer diameter and 0.50 mm inner diameter. This test confirms the characteristic of high flexibility of the material described above. In Table 8 there are reported the load values (expressed in Newtons), which are obtained at preset lowering amount values for the feeler (1 to 8 mm).

TABLE 9

| | | Cross-beam displacement | | | | | | | |
| --- | --- | --- | --- | --- | --- | --- | --- | --- | --- |
| | Sample | 1 mm | 2 mm | 3 mm | 4 mm | 5 mm | 6 mm | 7 mm | 8 mm |
| Load (N) | 1 | 0.009 | 0.020 | 0.032 | 0.044 | 0.053 | 0.056 | 0.057 | 0.057 |
| | 2 | 0.014 | 0.027 | 0.038 | 0.050 | 0.057 | 0.060 | 0.062 | 0.062 |
| | 3 | 0.015 | 0.028 | 0.039 | 0.050 | 0.060 | 0.061 | 0.062 | 0.063 |
| | 4 | 0.015 | 0.028 | 0.043 | 0.051 | 0.062 | 0.067 | 0.073 | 0.070 |
| | 5 | 0.012 | 0.030 | 0.038 | 0.052 | 0.061 | 0.065 | 0.067 | 0.067 |
| | Average | 0.013 | 0.027 | 0.038 | 0.049 | 0.059 | 0.062 | 0.064 | 0.064 |

The table shows a maximum load point of 0.073 N at a feeler travel of 77 mm. This result is particularly significant as it points out the optimal flexural characteristics of the inventive material.

To better appreciate the high flexibility of the tube made of elastomeric material according to the present invention, a comparative test has been carried out with equally sized tubes made of a material widely used in the art. The results are reported in Table 10:

TABLE 10

|  | Displacement of cross-beam | mixture 2 average values | Grilamid FE7303 average values |
|---|---|---|---|
| Load (N) | 1 mm | 0.013 | 0.009 |
|  | 2 mm | 0.027 | 0.025 |
|  | 3 mm | 0.038 | 0.041 |
|  | 4 mm | 0.049 | 0.052 |
|  | 5 mm | 0.059 | 0.062 |
|  | 6 mm | 0.062 | 0.066 |
|  | 7 mm | 0.064 | 0.069 |
|  | 8 mm | 0.064 | 0.068 |
|  | Maximum load | 0.064 | 0.069 |

Tubes having the same size have been used for the comparative test. The wall thickness is 0.20 mm. The various materials have the same degree of hardness.

A tube made of material of mixture 2 has 70.5 Shore D hardness, 1066 Mpa flexural elastic module, 46.17 Mpa tensile strength at break and about 350% elongation at break.

In the compliance and flexibility tests, 31 balloon samples have been tested having 3 mm outer diameter at 7 bar rated pressure, with 0.0383 double average wall thickness.

The compliance test is carried out by measuring the diameter increase (in mm) of the balloon being tested as compared with the pressure increase (in bars) to burst pressure.

The most significant data obtained from this test are reported in Table 11. The reported data relate to the average burst pressure recorded, the standard deviation of the measurements performed and the RBP (Rated Burst Pressure) calculated.

TABLE 11

| Balloon diameter (mm) | 3 |
|---|---|
| Average wall thickness (mm) | 0.038 |
| Average burst pressure (bar) | 22.88 |
| Standard deviation | 0.38 |
| Calculated RBP (bar) | 20.91 |

Comparative tensile at break tests have been carried out also for mixture 2. The data obtained are reported in Table 12.

TABLE 12

|  | Load (N) | % Elongation |
|---|---|---|
| Mixture 2 | 23 | 125 |
| Grilamid FE7303 | 21 | 45 |

Balloons obtained with mixture 2 have a greater break resistance and a percentage elongation at break which are more than twice those obtained with prior art materials.

EXAMPLE 3

To better appreciate the characteristics of flexibility of the balloons made of elastomeric material of the present invention as compared with those of the prior art, comparative bounce flexibility tests have been carried out such as widely described above. 10 balloons have been used to carry out this test:

5 balloons made of a material as from mixture 1 (40% Pa12, 60% UBESTA XPA 9063™); 5 balloons made of a material widely used in the prior art.

The test has been carried out by mounting the balloons at the distal end of 10 catheters having the same technical characteristics. The catheters differ from each other only by the distal balloon. The results are reported in Table 13:

TABLE 13

|  | Sample | Cross-beam displacement | | | | | | | | Maximum value |
|---|---|---|---|---|---|---|---|---|---|---|
|  |  | 1 mm | 2 mm | 3 mm | 4 mm | 5 mm | 6 mm | 7 mm | 8 mm |  |
| Load (N) | 1 | 0.012 | 0.017 | 0.020 | 0.024 | 0.025 | 0.027 | 0.028 | 0.029 | 0.029 |
|  | 2 | 0.018 | 0.021 | 0.023 | 0.026 | 0.029 | 0.031 | 0.030 | 0.028 | 0.031 |
|  | 3 | 0.004 | 0.008 | 0.010 | 0.012 | 0.013 | 0.018 | 0.017 | 0.016 | 0.018 |
|  | 4 | 0.016 | 0.019 | 0.021 | 0.026 | 0.027 | 0.029 | 0.027 | 0.026 | 0.029 |
|  | 5 | 0.007 | 0.008 | 0.011 | 0.015 | 0.024 | 0.025 | 0.024 | 0.024 | 0.025 |
|  | 6 | 0.005 | 0.008 | 0.012 | 0.015 | 0.020 | 0.023 | 0.025 | 0.025 | 0.025 |
|  | 7 | 0.004 | 0.008 | 0.011 | 0.014 | 0.018 | 0.020 | 0.021 | 0.023 | 0.023 |
|  | 8 | 0.011 | 0.012 | 0.017 | 0.021 | 0.023 | 0.025 | 0.028 | 0.027 | 0.028 |
|  | 9 | 0.004 | 0.007 | 0.011 | 0.016 | 0.020 | 0.026 | 0.025 | 0.023 | 0.026 |
|  | 10 | 0.026 | 0.032 | 0.035 | 0.042 | 0.046 | 0.048 | 0.047 | 0.075 | 0.048 |

TABLE 14

| Legenda: | | | |
|---|---|---|---|
| Sample | Balloon diameter (mm) | Balloon length (mm) | material |
| 1 | 1.25 | 20 | mixture 1 (40% PA12/60% UBESTA XPA 9063 ™) |
| 2 | 1.25 | 20 | grilamid FE7303 |
| 3 | 1.50 | 20 | mixture 1 (40% PA12/60% UBESTA XPA 9063 ™) |
| 4 | 1.50 | 20 | grilamid FE7303 |
| 5 | 2.00 | 20 | mixture 1 (40% PA12/-60% UBESTA XPA 9063 ™) |
| 6 | 2.00 | 20 | grilamid FE7303 |
| 7 | 2.25 | 20 | mixture 1 (40% PA12/60% UBESTA XPA 9063 ™) |
| 8 | 2.25 | 20 | grilamid FE7303 |
| 9 | 2.50 | 20 | mixture 1 (40% PA12/60% UBESTA XPA 9063 ™) |
| 10 | 2.50 | 20 | grilamid FE7303 |

The test has been carried out with pairs of balloons having the same diameter, the same length but different constitutive materials.

As may be seen in the comparative test, the balloons made of a material according to the present invention are considerably more flexible than those made of prior art material.

As may be seen from the analysis of data, very high hardness values are obtained with these 2 mixtures of examples 1 and 2 (67.5 Shore D for mixture 1 with 40% PA 12 and 60% UBESTA XPA 9063™ and 70.5 Shore D for mixture 2 with 70% PA12 and 30% UBESTA XPA 9063™). Nevertheless, very high flexural values have been however obtained. This detail has emerged also from the comparative test reported in the example 3 by comparing different balloons. To those skilled in the art the reported values will clearly appear as significant in order to define the good compliance characteristic of the balloons according to the present invention. Particularly, the burst pressure data as stated above are significant in combination with the characteristic of good flexibility of the balloons. In fact, it can be deduced that the balloons being the object of the present invention have a compliance characteristic which is usually found in much less flexible materials. Furthermore, the novel balloons as described herein have the significant advantage of a greater burst pressure and hence a higher RBP, in addition to a less percentage diameter increase between the rated pressure and said RBP, as compared with those prior art balloons having comparable hardness characteristics.

Furthermore, the low value of standard deviation calculated on the tested balloon samples demonstrates the high uniformity of behaviour and characteristics of the balloons obtained with the novel material according to the present invention. Moreover, this data is an index of high reproducibility of the advantageous characteristics specific of the balloons being the object of the invention described herein.

The good compliance characteristics of the balloon obtained with the elastomeric material described in the present invention allow applying said balloons in the coronary therapy, because the risk of breaking the vessel due to a too high expansion of the balloon is low.

Those skilled in the art will readily understand that the elastomeric material being the object of the present invention can be also used for manufacturing medical devices for angioplasty, particularly catheters or parts thereof, such as tubes, balloons, connections, tips, etc.

Advantageously, it has been found that the elastomeric material being the object of the present invention can be also used in tubes and/or multi-layer balloons, i.e. consisting of layers made of different materials, with different mechanical characteristics. Particularly, tubes and balloons for catheters are known to be used, which consist of several layers of different materials (see for example patent WO 03/072177). The advantage of using multi-layer tubes and balloons is that different materials can be used for the inner and outer walls, these materials being selected based on their mechanical characteristics.

The invention claimed is:

1. An angioplasty balloon comprising a polymer mixture comprising a polyamide and from 10 to 90% by weight of an elastomeric material, characterized in that said elastomeric material comprises a polyamide-based polymer obtained from the polymerization of a compound forming polyamide blocks that is selected from the group consisting of an aminocarboxylic acid of Formula (1) and a lactam of Formula (2):

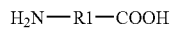
(1)

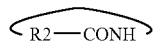
(2)

with a polyether diamine triblock compound of Formula (3):

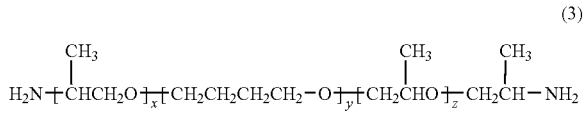
(3)

and a dicarboxylic acid of Formula (4):

$$HOOC-(R3)_m-COOH \quad (4)$$

wherein the groups R1, R2 and R3 are each binding groups comprising a hydrocarbon chain therein that may be interrupted by one or more amide groups; x is an integer from 1 to 20; y is an integer from 4 to 50, z is an integer from 1 to 20; m is 0 or 1;

wherein the angioplasty balloon is provided on a catheter, and wherein the angioplasty balloon is configured for inflation and deflation during an angioplasty operation.

2. The angioplasty balloon according to claim 1, wherein R1 and R2 independently comprise an alkylene group having 2 to 20 carbon atoms and amide bonds, R3 comprises an alkylene group having 1 to 20 carbon atoms, x is an integer from 1 to 18, y is an integer from 4 to 50, and z is an integer from 1 to 20.

3. The angioplasty balloon according to claim 1, wherein x, y and z are 3, 14, 2, respectively.

4. The angioplasty balloon according to claim 1, wherein said aminocarboxylic acid of Formula (1) and said lactam of Formula (2) are independently aliphatic, alicyclic or aromatic.

5. The angioplasty balloon according to claim 1, wherein said dicarboxylic acid (4) include dicarboxylic acids having 2 to 20 carbon atoms.

6. The angioplasty balloon according to claim 1, wherein said dicarboxylic acid (4) is synthesized by dimerization of unsaturated fatty acids.

7. The angioplasty balloon according to claim 1, wherein said lactams (2) include compounds having 5 to 20 carbon atoms.

8. The angioplasty balloon according to claim 1, wherein said amino-carboxylic acids (1) include aliphatic w-aminocarboxylic acids having 5 to 20 carbon atoms.

9. The angioplasty balloon according to claim 1, wherein the polyamide segment is selected from PA 6, PA 6/6, PA 6/9, PA 6/10, PA 6/12, PA 6/36, PA 11, PA 12 and PA 12/12, or is obtained from $C_2$-$C_{36}$ dicarboxylic acids and $C_2$-$C_{12}$ diamines, from monomers of $C_6$-$C_{12}$ lactams or monomers of $C_6$-$C_{12}$ aminocarboxylic acids.

10. The angioplasty balloon according to claim 1, wherein said polyamide-based polymer is represented by Formula (5):

$$HO-(OC-PA-CO-HN-Pe-NH)_n-H \quad (5)$$

wherein PA is the polyamide portion and Pe is a polyether portion, whereas n is the number of units forming the polymer.

11. The angioplasty balloon according to claim 10, wherein the molecular weight of said polyamide-based polymer ranges between 19000 and 50000.

12. The angioplasty balloon according to claim 1, wherein x is an integer from 2 to 6, y is an integer from 6 to 12, and z is an integer from 1 to 5.

13. The angioplasty balloon according to claim 1, wherein said polymerization is carried out using 15 to 70 wt % of said compound of Formula (1) and/or (2) and a mixture of said compounds of Formula (3) and (4), with total weight ranging from 30 to 85%.

14. The angioplasty balloon according to claim 13, wherein said polymerization is carried out by mixing said compounds of Formula (1) and/or (2), said compound of Formula (3) and said compound of Formula (4), by heating at a temperature ranging between 150 and 300° C.

15. The angioplasty balloon according to claim 13, wherein said polymerization is carried out by pre-polymerizing said compounds of formula (1) and/or (2) with said compound of Formula (4) and subsequently adding said compound of Formula (3) to the pre-polymer thus obtained, until the polymerization is completed.

16. The angioplasty balloon according to claim 1, wherein the dicarboxylic acid of Formula (4) is an aliphatic dicarboxylic acid.

17. The angioplasty balloon according to claim 1, wherein said polyamide-based elastomer is comprised in said elastomeric material in an amount from 75 to 25% by weight, the remaining part being polyamide.

18. The angioplasty balloon according to claim 17, wherein said polyamide-based elastomer is comprised in said elastomeric material in an amount from 60 to 40% by weight, the remaining part being polyamide.

19. The angioplasty balloon according to claim 1, wherein said polymer mixture comprising said polyamide and said elastomeric material is in multi-layer form.

20. The angioplasty balloon according to claim 1, wherein said polyamide is polyamide 12.

21. The angioplasty balloon according to claim 1, wherein said balloon has a diameter of 1.50 mm, a double average wall thickness lower than 0.023 mm.

22. The angioplasty balloon according to claim 1, wherein said balloon has a maximum flexural load lower than 0.040 N.

23. The angioplasty balloon according to claim 1, wherein said balloon has, at 2 mm diameter, an average burst pressure higher than 23 bar, and a calculated RBP higher than 20 bar.

24. The angioplasty balloon according to claim 19, wherein said balloon has a tensile strength at break higher than 5 N.

25. The angioplasty balloon according to claim 19, wherein said balloon has a percentage elongation at break higher than 30%.

* * * * *

UNITED STATES PATENT AND TRADEMARK OFFICE
CERTIFICATE OF CORRECTION

PATENT NO.        : 8,512,281 B2
APPLICATION NO. : 12/300475
DATED             : August 20, 2013
INVENTOR(S)       : Botticini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this

Fifteenth Day of September, 2015

Michelle K. Lee
*Director of the United States Patent and Trademark Office*